(12) United States Patent
Hendriks et al.

(10) Patent No.: US 8,360,963 B2
(45) Date of Patent: Jan. 29, 2013

(54) IMAGING SYSTEM WITH TWO IMAGING MODALITIES

(75) Inventors: Bernardus Hendrikus Wilhelmus Hendriks, Eindhoven (NL); Gert T Hooft, Eindhoven (NL); Stein Kuiper, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 838 days.

(21) Appl. No.: 12/519,766

(22) PCT Filed: Dec. 17, 2007

(86) PCT No.: PCT/IB2007/055147
§ 371 (c)(1),
(2), (4) Date: Jun. 18, 2009

(87) PCT Pub. No.: WO2008/078254
PCT Pub. Date: Jul. 3, 2008

(65) Prior Publication Data
US 2009/0264707 A1    Oct. 22, 2009

(30) Foreign Application Priority Data

Dec. 22, 2006  (EP) .................................... 06127127
Feb. 2, 2007  (EP) .................................... 07101679

(51) Int. Cl.
*A61B 1/06*    (2006.01)
(52) U.S. Cl. ..................................................... 600/160
(58) Field of Classification Search .................. 606/1–3; 600/160, 167, 174, 178, 180, 182
See application file for complete search history.

(56) References Cited

U.S. PATENT DOCUMENTS

| | | | |
|---|---|---|---|
| 5,975,697 | A | 11/1999 | Podoleanu et al. |
| 6,485,413 | B1 | 11/2002 | Boppart et al. |
| 7,126,903 | B2 | 10/2006 | Feenstra et al. |
| 2003/0229270 | A1 | 12/2003 | Suzuki et al. |

FOREIGN PATENT DOCUMENTS

| | | |
|---|---|---|
| EP | 1299711 | 1/2002 |
| EP | 1441215 | 7/2004 |
| EP | 1441215 A1 * | 7/2004 |
| WO | WO2005082225 | 9/2005 |

OTHER PUBLICATIONS

Xie et al., "GRIN Lens Rod Based Probe for Endoscopic Spectral Domain Optical Coherence Tomography With Fast Dynamic Focus Tracking", Optics Express, vol. 14, No. 8, Apr. 17, 2006, pp. 3238-3246, XP002480445.

(Continued)

*Primary Examiner* — Melanie Hand

(57) ABSTRACT

An imaging system with two modalities has a catheter with an optical lens system situated at an end of the catheter and optically connected to optical guide. The lens system has a numerical aperture which is changeable between a first aperture and a second larger numerical aperture. The imaging system also has an imaging unit for optical imaging with the catheter. First and second imaging modalities are optically connectable with the optical lens system of the catheter. The imaging system can change between imaging in two modes: (1) the first numerical aperture of the optical lens system and the first imaging modality of the imaging unit, and (2) the second numerical aperture of the optical lens system and the second imaging modality of the imaging unit.

15 Claims, 6 Drawing Sheets

OTHER PUBLICATIONS

Madjid et al., "Finding Vulnerable Arterosclerotic Plaques: Is it Worth the Effort", Arterioscler. Throm. Vasc. Viol. 24 (2004), pp. 1775-1782.
Gobel, W., Opt. Lett., vol. 29 (2004), pp. 1285-1287.
Postma et al., Review of Scientific Instruments, 76 (2005) 123105.
Pawley, J.B., Handbook of Confocal Microscopy, Chapter 28, ISBM 10:0-387-25921-X, Publisher: Springer.
Tearney et al., "Scanning Single-Mode Fibre Optic Catheter-Endoscope for Optical Coherence Tomography", Opt. Lett. 21 (1996), pp. 543-545.

* cited by examiner

IMAGING SYSTEM WITH TWO IMAGING MODALITIES

FIELD OF THE INVENTION

The present invention relates to an imaging system with two or more imaging modalities, a corresponding catheter, a corresponding imaging unit, and a corresponding method.

BACKGROUND OF THE INVENTION

Interventional imaging of patients is an area of promising progress. Catheter-based treatments in the cardiovascular field, such as stent placing and aneurism treatment, are exceeding several million interventions per year. The benefits of these minimal invasive techniques compared to open surgery are numerous. To further reduce the risks for the patients during interventions and to open up new catheter-based treatments, the local diagnosis of the diseased cardiovascular tissue must be further improved.

Arteriosclerosis (plaque) forms an important disease affecting millions of people. Among the various types of plaque, the vulnerable plaque (sometimes call high-risk plaque) is the life threatening form, which is responsible for about 70% of fatal acute myocardial infarction and/or sudden deaths. Diagnosing and treating vulnerable plaque are both important in this respect because it requires a complete care cycle, hence there is no opportunity for treatment without diagnosis and vice versa.

Optical techniques have the unique properties of allowing detailed molecular and structural analysis of tissue while being compact and minimally invasive if integrated in catheters. For example, when a disease like arteriosclerosis is detected, knowledge of its severeness is important in order to be able to select the optimal treatment. This requires a more detailed knowledge of the diseased area. This detailed plaque inspection cannot be performed properly with current techniques like conventional angiography, magnetic resonance angiography (MRA) or computed tomographic angiography (CTA). Optical techniques are highly suitable for obtaining detailed molecular and structural information, and will improve the treatment.

Although various modalities exist to characterize plaque, methods to get detailed information in vivo on the cellular and molecular level of plaque are still underdeveloped. There are various modalities that can characterize vulnerable plaque to a certain extend (see for example Madjid et al., "*Finding vulnerable arterosclerotic plaques: Is it worth the effort*", Arterioscler. Thromb. Vasc. Biol. 24 (2004) pp. 1775-1782.), but they are not able to characterize in-vivo the plaque on a cellular/molecular level.

EP1299711 discloses a method and an apparatus for examining the sub-surface microstructure of an in-vivo sample, in particular with optical coherence tomography (OCT). Radiation from a plurality of optical radiation sources travels along a first optical path. In the first optical path, a device focuses the optical radiation from each of the optical sources into a plurality of respective focal points along the first optical path to provide substantially continuous coverage of a selected portion of the first optical path. Then, a sample on the first optical path within the selected length extending into the sample is scanned along said selected portion of the first optical path and an image of the sample being examined can be obtained. This provides a solution to the problem of performing a fast scanning by OCT by a somewhat complicated lens system with multiple fibre/channels stepped in relation to one another, cf. FIGS. 1 and 2. However the lens geometry is fixed making such devices quite inflexible with respect to change of imaging depth and/or imaging technique. Another aspect of scanning the area of interest at high resolution only is that the required measuring time becomes rather large. Furthermore, OCT only provides only limited molecular information of tissue.

Hence, an improved imaging system would be advantageous, and in particular a more efficient and/or reliable imaging system for in-vivo imaging and characterization would be advantageous.

SUMMARY OF THE INVENTION

Accordingly, the invention preferably seeks to mitigate, alleviate or eliminate one or more of the above mentioned disadvantages singly or in any combination. In particular, it may be seen as an object of the present invention to provide an imaging system that solves the above mentioned problems of the prior art with inflexible imaging.

This object and several other objects are obtained in a first aspect of the invention by providing an imaging system comprising:

a catheter having an optical lens system, the optical lens system being situated at an end portion of the catheter and optically connected to optical guide means for guiding light through the catheter, the optical lens system having a numerical aperture which is changeable between a first numerical aperture (1NA) and a second numerical aperture (2NA), said second numerical aperture being higher than said first numerical aperture, and an imaging unit being arranged for optical imaging in co-operation with the catheter, the imaging unit comprising a first imaging modality (1IM) and a second imaging modality (2IM), both imaging modalities being optically connectable with the optical lens system of the catheter, wherein the imaging system is capable of changing between imaging with 1) the first numerical aperture (1NA) of the optical lens system and the first imaging modality (1IM) of the imaging unit, and
2) the second numerical aperture (2NA) of the optical lens system and the second imaging modality (2IM) of the imaging unit.

The invention is particularly, but not exclusively, advantageous for obtaining an imaging system that may provide fast and/or flexible imaging for in-vivo imaging as the change between the first and the second imaging modality can be performed quite fast, and accordingly the first and second imaging modality can be chosen so as to complement each other. In particular, the invention may be suitable for facilitating an imaging system where dual imaging is performed at a site of interest, where initially the first imaging modality may provide an overview of the site of interest, and subsequently the second imaging modality may provide a more detailed imaging of selected areas and/or regions, the selected areas and/or regions may for example be indicated or selected from the first imaging modality. The two measurements may be performed sequentially or performed during one measurement where a constant switching between one mode and the other mode occurs.

Furthermore, the present invention is particularly, but not exclusively, advantageous for obtaining an imaging system with a plurality of imaging modalities that may have a relatively simple optical and mechanical construction despite the plurality of imaging modalities. Prior art solutions, e.g. EP1299711, have used multiple optical channels which both makes the mechanical and/or optical design more complicated, and it also makes it difficult to design the catheter small enough to access minute tissue of interest for diagnostic purposes. Miniaturisation is accordingly a key parameter, in particular for examination of possible arteriosclerosis (plaque) and similar diseases, and it is therefore important to have a sufficiently small catheter of the imaging system.

Within the context of the present invention, a definition of catheter may be a substantially tubular medical device for insertion into canals, vessels, passageways, or body cavities. Additionally, a catheter usually keeps a passage open and/or may permit injection or withdrawal of fluids, which in particular may be performed for providing imaging access to the tissue of interest.

Within the context of the present invention, an imaging modality may be defined as an entity implemented in any suitable form including hardware, software, firmware or any combination of these, the entity applying a physical principle of optical interaction with the object being imaging, the optical interaction resulting in an optical feedback from which an image and/or characterization representative of the object can be obtained. Advantageously, a focal length of the optical lens system may change accordingly with the change between the first numerical aperture (1NA) and the second numerical aperture (2NA). For a fixed entrance pupil diameter of a lens, a reciprocal relation is present between the numerical aperture and the focal length. The change of focal length offers in particular depth imaging. However, the present invention may also be implemented by changing an entrance pupil diameter e.g. by a diaphragm without changing the focal length. Possibly, a combination of changing both the focal length and the entrance pupil diameter can be applied within the context of the present invention.

Beneficially, the catheter may comprise first control means arranged for changing the numerical aperture of the optical lens system between the first numerical aperture (1NA) and the second numerical aperture (2NA), e.g. dedicated conductors within the catheter may supply power and control the adjustable part of the lens system. Similarly, the imaging unit may comprise second control means arranged for changing between imaging with the first (1IM) and the second (2IM) imaging modalities of the imaging unit, and the first and second control means then further being arranged for mutual interaction, e.g. synchronisation, with respect to change of imaging i.e. changing of imaging mode. This can provide a reliable coordination between the catheter and the image unit.

In one embodiment, the changeable numerical aperture between the first numerical aperture (1NA) and the second numerical aperture (2NA) is provided by an active optical component. An active optical component can be defined as an optical component having optical parameters changeable upon external influence on the component, e.g. by electrical or acoustical means etc., but not a movement of the optical component. This further enables miniaturisation and efficient control of the optical lens system. The optical lens system may for example comprise a liquid lens so as to provide a numerical aperture which is changeable between the first numerical aperture (1NA) and the second numerical aperture (2NA), the liquid lens facilitating both gradual changes in the numerical aperture or fast and/or abrupt changes in the numerical aperture. Alternatively, the optical lens system may comprise a liquid crystal (LC) lens so as to provide a numerical aperture which is changeable between the first numerical aperture (1NA) and the second numerical aperture (2NA).

In another embodiment, the optical lens system may comprise a set of lenses being relatively displaceable along an optical axis of the optical lens system so as to provide a numerical aperture which is changeable between the first numerical aperture (1NA) and the second numerical aperture (2NA). Thus, the set of lenses can be moved in relation to each other to provide a changeable numerical aperture. This offers a quite simple design though the dynamic range of numerical apertures available may be lower as compared to an active optical component when considering the available space within the catheter.

The first numerical aperture (1NA) may be below approximately 0.2, preferably below approximately 0.3, or more preferably below approximately 0.4. Alternatively, the first numerical aperture (1NA) may be below approximately 0.1 or below approximately 0.5.

The second numerical aperture (2NA) may accordingly be above approximately 0.4, preferably above approximately 0.5, or more preferably above approximately 0.6. Alternatively, the second numerical aperture (2NA) may be above approximately 0.7, preferably above approximately 0.8, or more preferably above approximately 0.9.

In an embodiment, the optical guide means may comprise a photonic crystal fibre (PCF) as these fibres have several optical advantages, in particularly a low dispersion.

Beneficially, the first imaging modality (1IM) may be an optical coherence tomography (OCT) imaging system offering millimeter penetration into tissue. Any suitable OCT variation such as time domain or frequency domain OCT may be applied. For frequency domain OCT, time encoded or spatially encoded frequency domain may be applied.

Advantageously, the second imaging modality may be a multi photon microscopy (MPM) imaging system. Alternatively, the second imaging modality may be a confocal microscopy (CM) imaging system. In particular, the confocal microscopy imaging system may be adapted for fluorescence detection.

In an embodiment, the first (1IM) and second (2IM) imaging modality may utilize a common radiation source. The radiation source may beneficially be a laser source, more particularly a femtosecond laser source.

In a second aspect, the present invention relates to a catheter having an optical lens system, the optical lens system being situated at an end portion of the catheter and optically connected to optical guide means for guiding light through the catheter, the optical lens system having a numerical aperture which is changeable between a first numerical aperture (1NA) and a second numerical aperture (2NA), said second numerical aperture being higher than said first numerical aperture, wherein the catheter is further adapted to be optically connected to an associated imaging unit arranged for optical imaging in co-operation with the catheter, the imaging unit comprising a first imaging modality (1IM) and a second imaging modality (2IM), both imaging modalities being optically connectable with the optical lens system of the catheter.

Beneficially, the catheter may comprise first control means arranged for changing the numerical aperture of the optical lens system between a first numerical aperture (1NA) and a second numerical aperture (2NA), and the associated imaging unit comprises second control means arranged for changing between imaging with the first (1IM) and second (2™) imaging modalities of the imaging unit, said first and second control means further being arranged for mutual interaction with respect to change of imaging.

In a third aspect, the present invention relates to a imaging unit arranged for optical imaging in co-operation with an associated catheter, the imaging unit comprising a first imaging modality (1IM) and a second imaging modality (2IM), both imaging modalities being optically connectable with the optical lens system of the catheter, the associated catheter having an optical lens system, the optical lens system being situated at an end portion of the catheter and optically connected to optical guide means for guiding light through the catheter, the optical lens system having a numerical aperture which is changeable between a first numerical aperture (1NA) and a second numerical aperture (2NA), said second numerical aperture being higher than said first numerical aperture, wherein the imaging unit is arranged for changing between imaging with
1) the first numerical aperture (1NA) of the optical lens system in the associated catheter and the first imaging modality (1IM), and
2) the second numerical aperture (2NA) of the optical lens system in the associated catheter and the second imaging modality (2IM).

In a fourth aspect, the present invention relates to a method for imaging with an imaging system, the method comprising:
providing a catheter having an optical lens system, the optical lens system being situated at an end portion of the catheter and optically connected to optical guide means for guiding light through the catheter, the optical lens system having a numerical aperture which is changeable between a first numerical aperture (1NA) and a second numerical aperture (2NA), said second numerical aperture being higher than said first numerical aperture, and
providing an imaging unit being arranged for optical imaging in co-operation with the catheter, the imaging unit comprising a first imaging modality (1IM) and a second imaging modality (2™), both imaging modalities being optically connectable with the optical lens system of the catheter,
wherein the method comprises changing between imaging with
1) the first numerical aperture (1NA) of the optical lens system and the first imaging modality (1IM) of the imaging unit, and
2) the second numerical aperture (2NA) of the optical lens system and the second imaging modality (2IM) of the imaging unit.

The first, second, third and fourth aspect of the present invention may each be combined with any of the other aspects. These and other aspects of the invention will be apparent from and elucidated with reference to the embodiments described hereinafter.

BRIEF DESCRIPTION OF THE FIGURES

The present invention will now be explained, by way of example only, with reference to the accompanying Figures, where.

DETAILED DESCRIPTION OF AN EMBODIMENT

Figure 1:
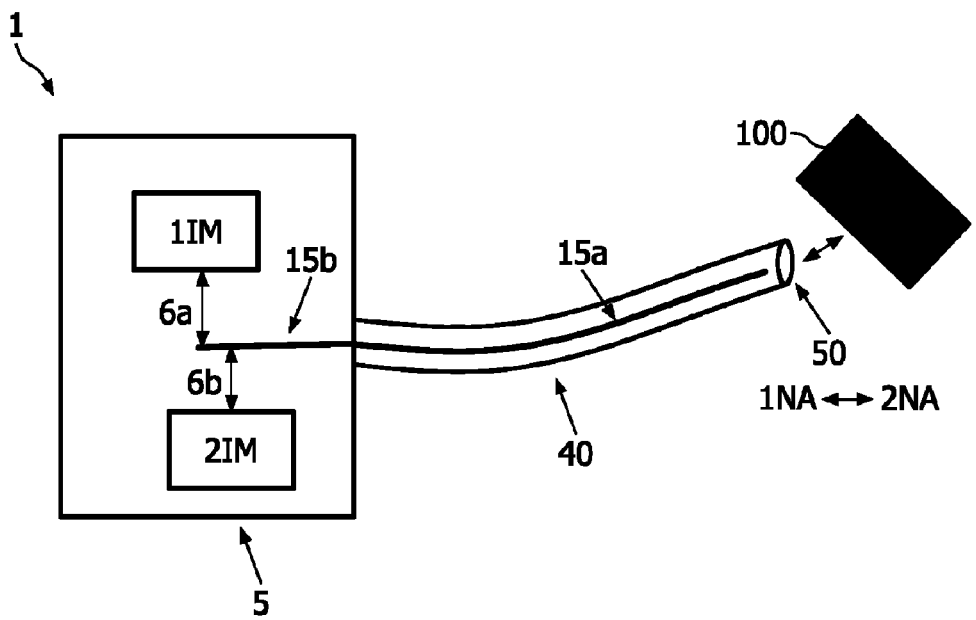
FIG. 1 is a schematic drawing of the imaging system according to the present invention.

FIG. 1 is a schematic drawing of the imaging system 1 according to the present invention. The imaging system 1 comprises two main parts, i.e. a catheter 40 and an imaging unit 5. The catheter 40 and the imaging unit 5 can be disconnected. Typically, the catheter 40 is disposable after one-time use, but the catheter 40 can also be reusable if the catheter 40 is suited for sufficiently hygienic cleaning.

The catheter has an optical lens system 50, which is situated at an end portion of the catheter 40. The lens system 50 is optically connected to optical guide means 15a for guiding light through the catheter 40. The optical lens system 50 has a numerical aperture NA, which is changeable between a first numerical aperture 1NA and a second numerical aperture 2NA as indicated in the Figure. The second numerical aperture 2NA is higher than the first numerical aperture 1NA: 2NA>1NA.

The imaging unit 5 is arranged for optical imaging in co-operation with the catheter 40. The imaging unit 5 comprises a first imaging modality 1IM and a second imaging modality 2IM as indicated in the Figure. Both imaging modalities 1IM and 2IM are optically connected through optical guide means 15b, and branches 6a and 6b, respectively, of the optical guide means 15b, with the optical lens system 50 of the catheter 40. The optical branches 6a and 6b may comprise closing means such as shutters or filters (see below) for controlling the imaging process.

The imaging system 1 is capable of changing between imaging of sample 100 with
1) the first numerical aperture 1NA of the optical lens system 50 and the first imaging modality 1IM of the imaging unit 5, and
2) the second numerical aperture 2NA of the optical lens system 50 and the second imaging modality 2IM of the imaging unit 5.

Figure 2:
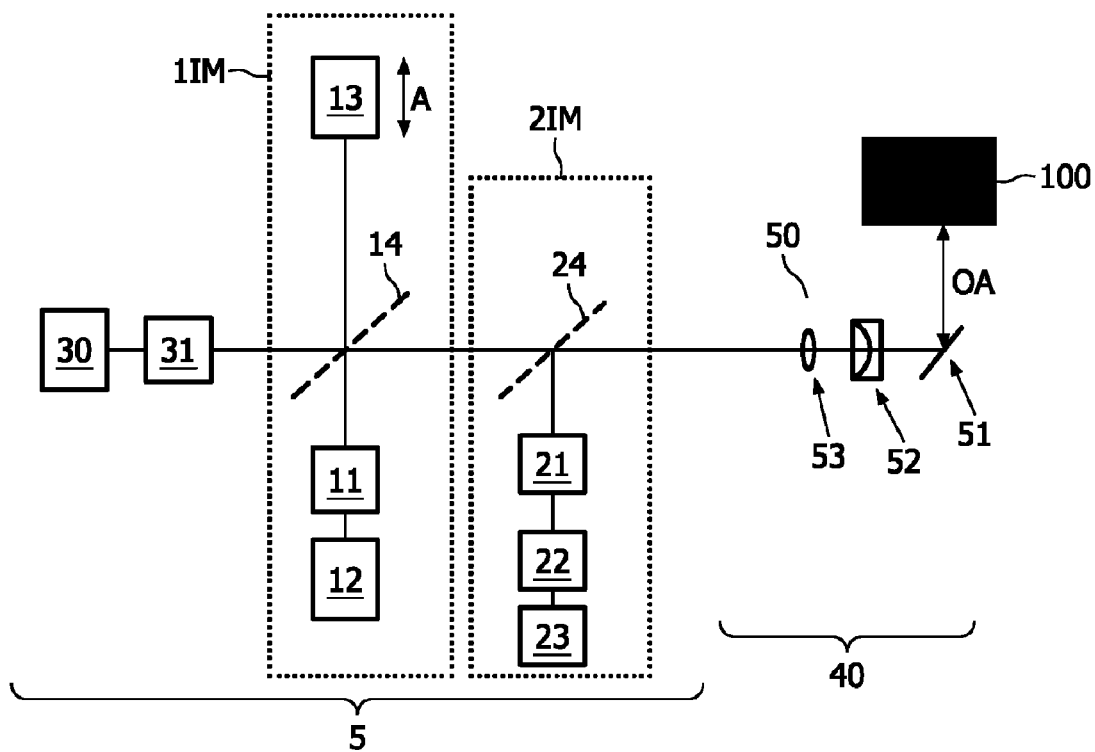
FIG. 2 is a schematic drawing of an embodiment according to the present invention.
Figure 3A:
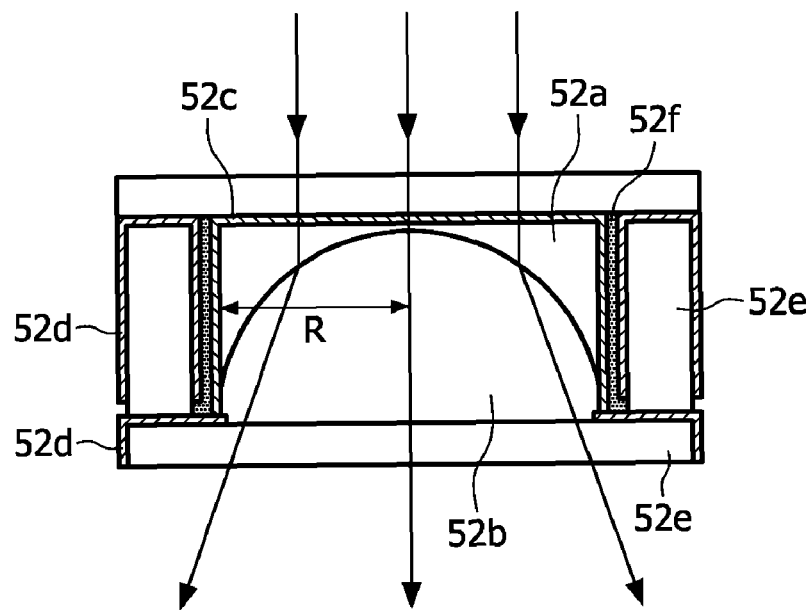
FIG. 3 is an illustrative drawing of the operation of a liquid lens with changeable numerical aperture.
Figure 3B:
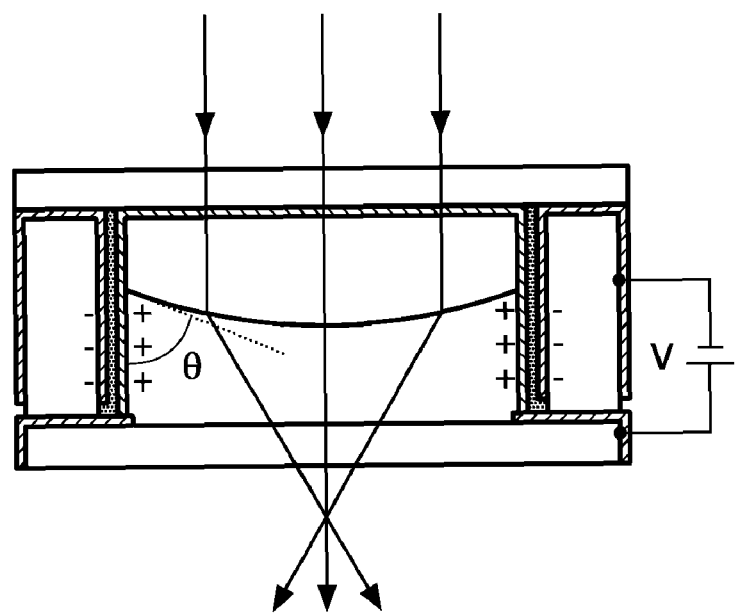
Figure 3E:
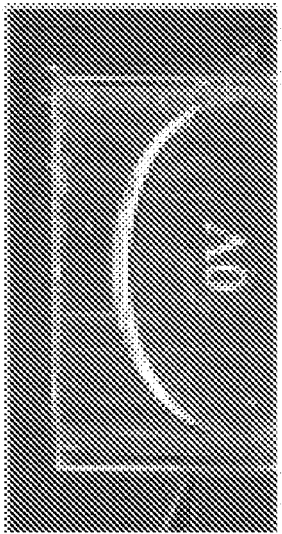
Figure 3D:
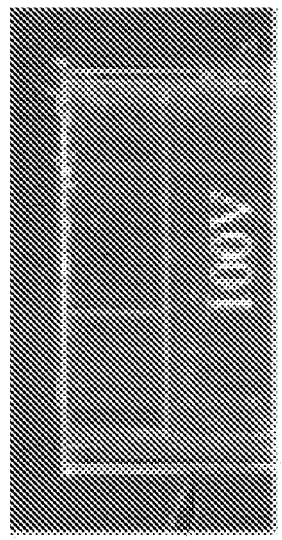
Figure 3C:
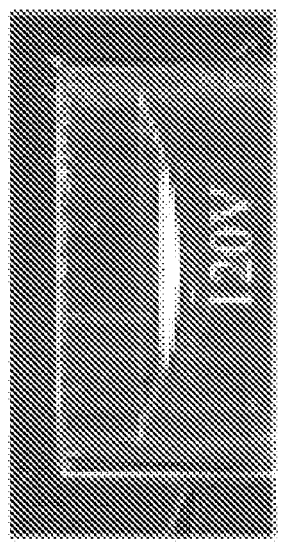

FIG. 2 is a schematic drawing of an embodiment according to the present invention showing the optical paths of an imaging system with again an imaging unit 5 (left) and a catheter 40 (right) with an optical lens system 50 comprising a focussing lens 53, a liquid lens 52 with an adjustable numerical aperture (cf. FIG. 3 below), and a combined lens and mirror 51.

The imaging system 1 of FIG. 2 has as a first imaging modality 1IM an optical coherence tomography modality (OCT), and as a second imaging modality 2IM a multiphoton microscopy (MPM) modality.

A femtosecond laser pulse source, e.g. a 12-fs Ti:sapphire laser with spectral bandwidth of 100 nm, central wavelength 800 nm, functions as a common radiation source 30 for the two imaging modalities 1IM and 2IM.

The output of the radiation source 30 passes a dispersion compensation element 31 (for instance a pair of fused silica Brewster prisms). As a result, the dispersion accumulated later in the imaging system 1 is pre-compensated. The light beam is transmitted through a partial beam splitter 14 and directed towards a dichroic mirror 24. The other part of the light is transmitted to an actuated mirror 13 that forms the reference arm of the optical coherence system in the first imaging modality 1IM. The mirror 13 is displaceable in the direction of the arrow A as indicated in FIG. 2.

The light beam that has been transmitted by the dichroic mirror 24 is coupled into the light guide means 15a (cf. FIG. 1) of the catheter 40, which may be an optical fibre. The optical fibre of the catheter 40 can in particular be a photonic crystal fibre with a hollow core, see for example W. Gobel, Opt. Lett. Vol. 29 (2004) pp. 1285-1287. The hollow core fibre has the main advantage that the main part of the optical energy propagates in air. This means that optical losses are reduced, but more importantly non-linear optical effects (second harmonic generation, soliton forming, stimulated Raman and Brillouin effects) are strongly reduced. The dispersion of the fibre is similar in magnitude as for normal fused silica, i.e. 200 ps/nm/km. For a sub 20 fs pulse with a bandwidth of say 80 nm and a fibre length of 1 m, this results in an additional chirp of 16 ps. This shows the relevance of the dispersion compensator 31.

The light coupled into the catheter 40 initially exits the optical fibre, and then passes focussing lens 53, and subsequently a liquid lens 52 that enables focus for the multiphoton detection mode (MPM) and lowers the numerical aperture for the OCT detection mode. As the light exits the optical guide means 15a (cf. FIG. 1), it results in a divergent beam depending on the exit numerical aperture of the fibre. This divergent point source beam is then collected by the fixed collimator lens 53, which transforms the beam into a substantially parallel beam.

After the liquid lens 52, a combined objective and fold mirror 51 is present that focuses the beam substantially sideways of the catheter 40 into the sample 100. For scanning in the direction of the optical axis OA (denoted as z-scan), the liquid lens 52 is used in the MPM detection mode. For the OCT detection no z-scanning is required, because this is taken care of by the reference arm and the mirror 13. The numerical aperture NA in the OCT mode must therefore be low enough to have sufficient focal depth to allow enough resolution during the z-scan performed by the reference arm of the OCT system of the first imaging modality 1IM. Light emitted or reflected back by the sample or tissue 100 is collected by the fold mirror/objective combination 51 and transmitted back via the optical fibre into the catheter 40 and the imaging unit 5.

When the imaging system 1 is in the multiphoton microscopy MPM detection mode, the fluorescence light is reflected by the dichroic mirror 24 through a filter 21 onto the fluorescence detector 22. This detector is coupled to an analyzing unit 23 that transforms the signal into a MPM data set, which can be transformed into an MPM image by appropriate analyzing of the data set.

It should be noted that the dispersion of the reference arm and the detector arm of the OCT in the first imaging modality 1IM must be very well balanced in order not to get any so-called ghost appearances in the obtained image. This can be obtained by using the same type of fibre and fibre lengths in both arms of the OCT interferometer. Additionally, a high-resolution spectral phase shaper may be incorporated in the reference arm to adjust the phase difference as a function of the wavelength. Such a device is described e.g. by S. Postma et al. in Review of Scientific Instruments, 76 (2005) 123105. The OCT detector is then coupled to an analyzing unit that transforms the signals into OCT data set and a corresponding image.

Instead of the time-domain implementation for OCT described above, where the reference mirror 13 is moved, also spectral-domain OCT can be employed in the present invention. In this case, the reference OCT arm is no longer moved during an axial OCT scan, but the simple OCT detector 12 is replaced by a more complicated detector consisting of a dispersive element, such as a diffractive grating, that diffracts the beam coming from reference OCT arm and coming back from the tissue 100, a lens that projects this diffracted beam onto a CCD camera. Finally, a processing unit translates this signal into an axial scan line. In the spectral-domain OCT, no longer axial scans have to be made, only scans are to be made in the lateral direction. Spectral-domain OCT has advantages with respect to time-domain in terms of acquisition speed and sensitivity. Alternatively, a fast laser scanning can be employed.

For the design of the optical lens system 50 with OCT and MPM modalities, two aspects are important. For two-photon imaging the two-photon absorbance probability $P_a$ is given by $$P_a = \delta \langle P \rangle^2 F_p^{-1} \left( \frac{\pi NA^2}{2\pi \hbar c \lambda} \right)^2 \xi \qquad (1)$$

where
$\delta$=two-photon cross section
$\langle P \rangle$=averaged laser power
$F_p$=repetition frequency laser
NA=numerical aperture objective system
$\lambda$=wavelength
c=speed of light
$\hbar$=Planck constant
$\xi$=two-photon advantage factor 1/(pulse width×repetition frequency laser)=1/duty cycle
(see Handbook of Confocal Microsocopy, chapter 28, editor J. B. Pawley, ISBN 10: 0-387-25921-X, Publisher: Springer). It is important in this respect that the NA should be as high as possible because the probability depends on $NA^4$. Typically, the numerical aperture should be NA>0.4.

For OCT the focal depth is of importance because this determines the scan depth. The lateral resolution is $\Delta r$ (=spot diameter), and it is given by $$\Delta r = 1.22 \frac{\lambda}{NA} \qquad (2)$$

where
NA=numerical aperture objective system
$\lambda$=wavelength
Furthermore, the focal depth $\Delta z$, hence the distance along the optical axis where the resolution is determined by the diffraction limit (see equation (2)), is given by $$\Delta z = \frac{2\lambda}{NA^2} \qquad (3)$$

Finally, the axial resolution is determined by the coherence length $l_c$ of the laser, which in turn is determined by the bandwidth of the laser $\Delta \lambda$ and wavelength $\lambda$ of the laser according to the relation $$l_c = \frac{2(\ln 2)\lambda^2}{\pi \Delta \lambda} \qquad (4)$$

Let us assume a lateral resolution of 40 μm at 800 nm. This requires a numerical aperture of NA=0.038. The corresponding focal depth is $\Delta z$=1.11 mm. So typically, the numerical aperture should be NA<0.1 resulting in a focal depth of $\Delta z$>0.160 mm. For a 12-femtosecond laser we have a bandwidth of 90 nm, which yields an axial resolution of $l_c/2$=1.6 μm.

FIG. 3 is an illustrative drawing of the operation of a liquid lens 52 with changeable numerical aperture NA. The light beam passes from above through a switchable liquid lens as indicated in the Figure. A switchable lens can be made according to the principles described in U.S. Pat. No. 7,126,903 B2 (Variable Focus Lens), which is hereby incorporated by reference in its entirety. In this reference, it is described how a variable-focus lens can be made with the smallest possible outer diameter. Such a small-diameter lens is obtained by placing two immiscible liquids in a short tube with an upper hydrophobic coating 52c and an insulating layer 52f. The two liquids have different refractive indices and therefore the meniscus between them forms a lens. By altering the curvature of the meniscus, the optical power of the lens can be varied. In FIG. 3, the working principle of a liquid lens is demonstrated in five parts. In part (a), the lens is in the off-state (no voltage applied), the interface between the two liquids 52a (insulating) and 52b (conducting) forms a half-sphere. In part (b), the lens is under application of a voltage on the electrodes 52d, and the interface changes curvature. In FIG. 3, parts (c), (d), and (e), are shown photographs of a liquid lens in action. The lens has a diameter of 6 mm, but diameters down well below 1 mm are possible.

From calculations it follows that the liquids 52a and 52b should have a fairly large difference in refractive index. A suitable combination could be a high-refractive index phenylated silicone oil in combination with water (n=1.333). An example of such an oil is 1,1,5,5-tetraphenyl-1,3,3,5-tetramethyltrisiloxane with refractive index 1.551. This oil is inert and fairly harmless to the human body. If a stronger optical power variation is required, it is possible to switch the lens further than flat, i.e. with a reverse curvature as it is shown in FIG. 3 (e), or it is possible to use two liquid lenses in series.

Figure 4:
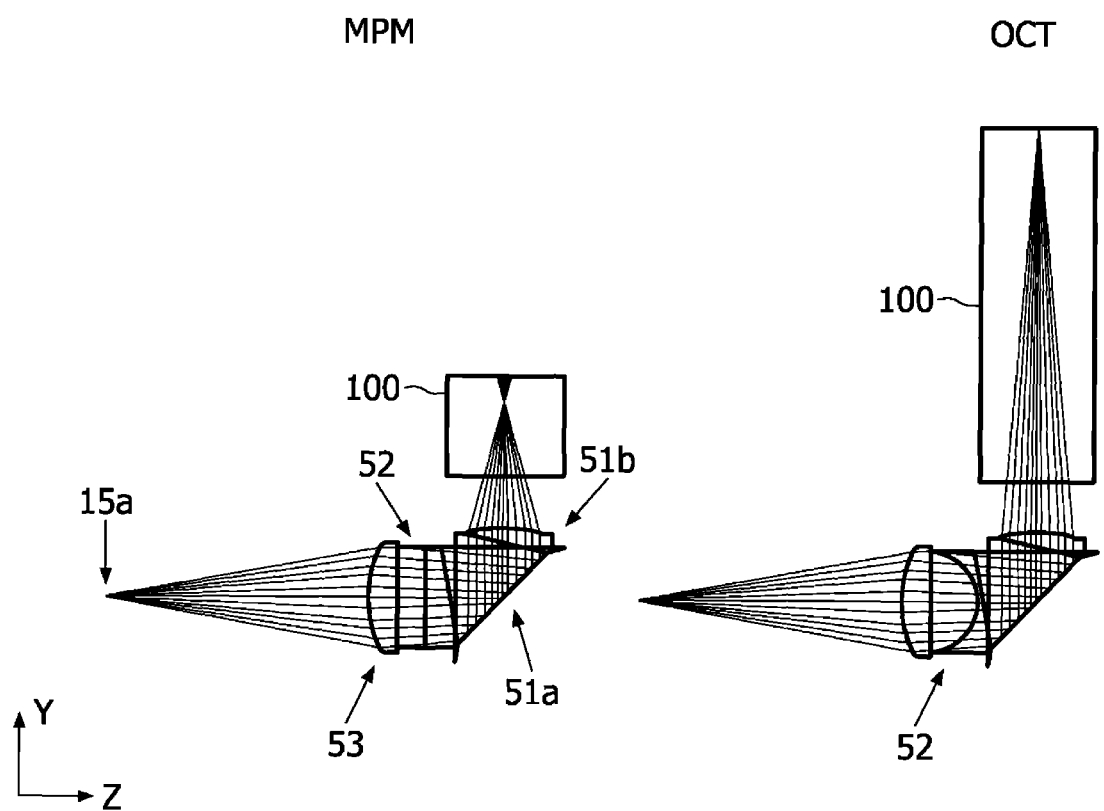
FIG. 4 is a schematic drawing of two optical paths in the optical lens system of the catheter according to the present invention.

FIG. 4 is a schematic drawing of two optical paths in the optical lens system 50 in the catheter 40. In the right hand part of FIG. 4, the optical lens system 50 is configured for the first OCT imaging modality, whereas in the left hand side of FIG. 4, the optical lens system 50 is configured for the second MPM imaging modality.

In the OCT readout mode (right part of FIG. 4), the liquid lens 52 is in the unswitched state, where the meniscus forms a half-sphere resulting in a diverging beam right behind the liquid lens and a slightly converging beam right behind the objective lens 51b. In this case, the numerical aperture of the image space is NA=0.1, while the beam is focused deep into the tissue 100 (a few millimeters). During the OCT scan with the mirror 13 of the OCT reference arm, the liquid lens 52 remains in the same switching state.

For MPM readout mode the liquid lens 52 is switched to a substantially flat state, resulting in a substantially parallel beam right behind the liquid lens and a strongly converging beam right behind the objective lens 51b. Consequently, the numerical aperture increases to NA=0.5, while the focal point of the system is now closer to a value so that the beam can be focused on the top layer of the tissue 100 (e.g. an interior wall of the artery). Switching or gradually changing the liquid lens 52 around the flat state enables focusing on different positions of the tissue 100. With MPM one can then inspect the first few hundred microns of the inner artery wall, providing both detailed morphological as well as functional information (molecular information). This is of particular interest when studying for instance vulnerable plaque.

In the OCT imaging mode, one can image the artery wall up to a few millimeters within the sample 100 giving detailed morphology and to a limited extend functional information (inhomogeneities in the refractive index). The combination of both OCT and MPM gives a detailed chemical knowledge of the vulnerable plaque layer as well as the surrounding morphology of the tissue 100.

Figure 5:
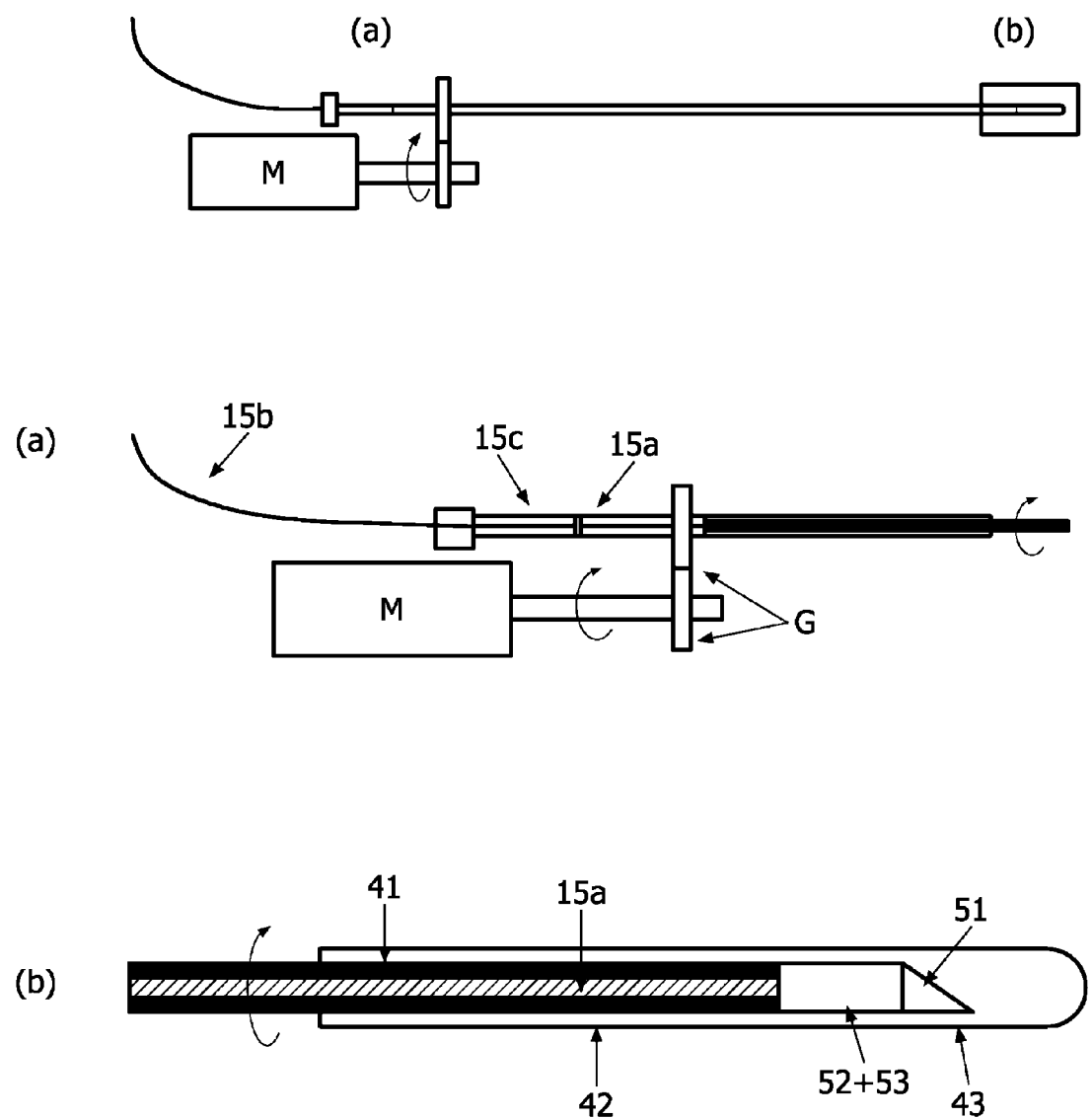
FIG. 5 is a schematic drawing of how the imaging system, in particular the catheter, can be operated according to the present invention.

FIG. 5 is a schematic drawing of how the imaging system 1, in particular the catheter 40, can be operated according to the present invention. To perform rotational scanning of the optical lens system 50 of the catheter 40, one makes use of a motor coupled to the fibre 15a, see e.g. G. Tearney et al., "Scanning single-mode fibre optic catheter-endoscope for optical coherence tomography", Opt. Lett. 21 (1996) pp. 543-545, or similar references.

In the proximal end (a) of the catheter 40, a motor M is arranged for rotating, via a set of suitable chosen gears G, the optical light guiding means 15a of the catheter. The optical light guiding means 15a is optically connected to the optical light guiding means 15b of the imaging unit 40 through an optical connector 15c, which is kept in a fixed position relative to the rotating guiding means 15a.

In the distal end (b) of the catheter 40, the optical light guiding means 15a is surrounded by an inner sleeve 41 that is rotated together with the optical fibre guiding means 15a. The catheter 40 comprises an outer sheath 42 that is not rotated together with the inner sleeve 41 because the outer sheath 42 constitutes an outermost surface of the catheter, which is in contact with a patient during in-vivo imaging. The inner sleeve 41 can comprise first control means (not shown) of the catheter, i.e. electric conductors to control the electrical voltage and/or current to the liquid lens 52.

The outer sheath 42 has a transparent window 43 positioned adjacent to the optical communication ports of the optical lens system 50, i.e. the window 43 should facilitate undisturbed optical access to the combined fold and mirror part 51.

Figure 6:
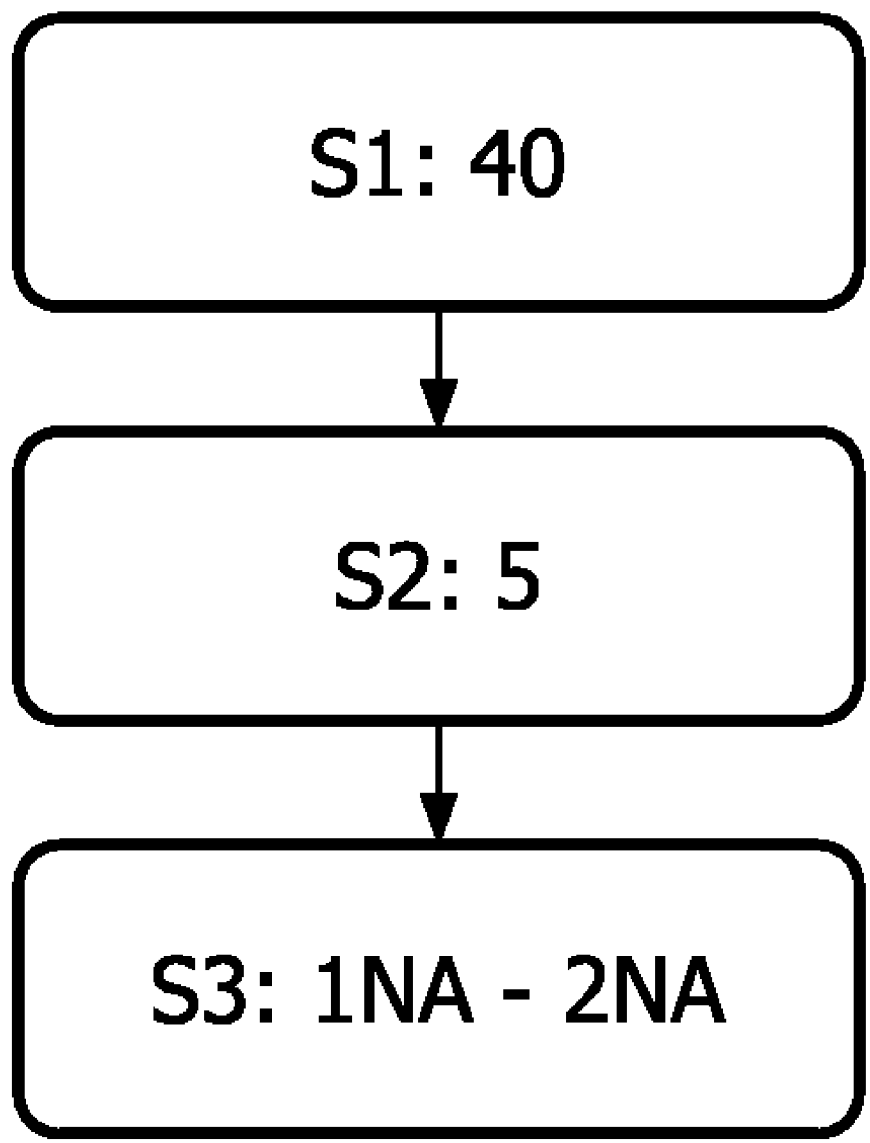
FIG. 6 is a flow-chart of a method according to the invention.

FIG. 6 is a flow-chart of a method according to the invention for imaging with an imaging system 1, the method comprising:

S1 providing a catheter 40 having an optical lens system 50, the optical lens system being situated at an end portion of the catheter and optically connected to optical guide means 15a for guiding light through the catheter, the optical lens system having a numerical aperture which is changeable between a first numerical aperture 1NA and a second numerical aperture 2NA, said second numerical aperture being higher than said first numerical aperture, and S2 providing an imaging unit 5 being arranged for optical imaging in co-operation with the catheter 40, the imaging unit comprising a first imaging modality 1IM and a second imaging modality 2IM, both imaging modalities being optically connectable with the optical lens system of the catheter, S3 the method comprises changing between imaging with two modes 1 the first numerical aperture (1NA) of the optical lens system and the first imaging modality (1IM) of the imaging unit, and 2 the second numerical aperture (2NA) of the optical lens system and the second imaging modality (2IM) of the imaging unit.

The invention can be implemented in any suitable form including hardware, software, firmware or any combination of these. The invention or some features of the invention can be implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. An imaging system comprising:
a catheter having an optical lens system, the optical lens system being situated at an end portion of the catheter and optically connected to optical guide unit configured to guide light through the catheter, the optical lens system having a numerical aperture which is changeable between a first numerical aperture and a second numerical aperture, said second numerical aperture being higher than said first numerical aperture, and
an imaging unit being arranged for optical imaging in co-operation with the catheter, the imaging unit comprising a first imaging modality and a second imaging modality, wherein the first and second imaging modalities are optically connectable with the optical lens system of the catheter,
wherein the imaging system is configured to change between imaging with:
the first numerical aperture of the optical lens system and the first imaging modality of the imaging unit, and
the second numerical aperture of the optical lens system and the second imaging modality of the imaging unit, and
wherein the catheter comprises a first control unit configured to change the numerical aperture of the optical lens system between the first numerical aperture and the second numerical aperture, and the imaging unit comprises a second control unit configured to change between imaging with the first and the second imaging modalities of the imaging unit, said first and second control units further being configured for mutual interaction with respect to change of the imaging.

2. The imaging system according to claim 1, wherein a focal length of the optical lens system is changed accordingly with the change between the first numerical aperture and the second numerical aperture.

3. The imaging system according to claim 1, wherein the changeable numerical aperture between the first numerical aperture and the second numerical aperture is provided by an active optical component.

4. An imaging system comprising:
a catheter having an optical lens system, the optical lens system being situated at an end portion of the catheter and optically connected to optical guide unit configured to guide light through the catheter, the optical lens system having a numerical aperture which is changeable between a first numerical aperture and a second numerical aperture, said second numerical aperture being higher than said first numerical aperture, and
an imaging unit being arranged for optical imaging in co-operation with the catheter, the imaging unit comprising a first imaging modality and a second imaging modality, wherein the first and second imaging modalities are optically connectable with the optical lens system of the catheter,
wherein the imaging system is configured to change between imaging with
the first numerical aperture of the optical lens system and the first imaging modality of the imaging unit, and
the second numerical aperture of the optical lens system and the second imaging modality of the imaging unit, and
wherein the optical lens system comprises a liquid lens so as to provide a numerical aperture which is changeable between the first numerical aperture and the second numerical aperture.

5. An imaging system comprising:
a catheter having an optical lens system, the optical lens system being situated at an end portion of the catheter and optically connected to optical guide unit configured to guide light through the catheter, the optical lens system having a numerical aperture which is changeable between a first numerical aperture and a second numerical aperture, said second numerical aperture being higher than said first numerical aperture, and
an imaging unit being arranged for optical imaging in co-operation with the catheter, the imaging unit comprising a first imaging modality and a second imaging modality, wherein the first and second imaging modalities are optically connectable with the optical lens system of the catheter,
wherein the imaging system is configured to change between imaging with
the first numerical aperture of the optical lens system and the first imaging modality of the imaging unit, and
the second numerical aperture of the optical lens system and the second imaging modality of the imaging unit, and
wherein the optical lens system comprises a liquid crystal lens so as to provide a numerical aperture which is changeable between the first numerical aperture and the second numerical aperture.

6. The imaging system according to claim 1, wherein the optical lens system comprises a set of lenses being relatively displaceable along an optical axis of the optical lens system so as to provide a numerical aperture which is changeable between the first numerical aperture and the second numerical aperture.

7. An imaging system comprising:
a catheter having an optical lens system, the optical lens system being situated at an end portion of the catheter and optically connected to optical guide unit configured to guide light through the catheter, the optical lens system having a numerical aperture which is changeable between a first numerical aperture and a second numerical aperture, said second numerical aperture being higher than said first numerical aperture, and
an imaging unit being arranged for optical imaging in co-operation with the catheter, the imaging unit comprising a first imaging modality and a second imaging modality, wherein the first and second imaging modalities are optically connectable with the optical lens system of the catheter,
wherein the imaging system is configured to change between imaging with
the first numerical aperture of the optical lens system and the first imaging modality of the imaging unit, and the second numerical aperture of the optical lens system and the second imaging modality of the imaging unit, and wherein the first numerical aperture is below approximately 0.4.

8. An imaging system comprising:

a catheter having an optical lens system, the optical lens system being situated at an end portion of the catheter and optically connected to optical guide unit configured to guide light through the catheter, the optical lens system having a numerical aperture which is changeable between a first numerical aperture and a second numerical aperture, said second numerical aperture being higher than said first numerical aperture, and an imaging unit being arranged for optical imaging in co-operation with the catheter, the imaging unit comprising a first imaging modality and a second imaging modality, wherein the first and second imaging modalities are optically connectable with the optical lens system of the catheter, wherein the imaging system is configured to change between imaging with the first numerical aperture of the optical lens system and the first imaging modality of the imaging unit, and the second numerical aperture of the optical lens system and the second imaging modality of the imaging unit, and wherein the second numerical aperture is above approximately 0.4.

9. An imaging system comprising:

a catheter having an optical lens system, the optical lens system being situated at an end portion of the catheter and optically connected to optical guide unit configured to guide light through the catheter, the optical lens system having a numerical aperture which is changeable between a first numerical aperture and a second numerical aperture, said second numerical aperture being higher than said first numerical aperture, and an imaging unit being arranged for optical imaging in co-operation with the catheter, the imaging unit comprising a first imaging modality and a second imaging modality, wherein the first and second imaging modalities are optically connectable with the optical lens system of the catheter, wherein the imaging system is configured to change between imaging with the first numerical aperture of the optical lens system and the first imaging modality of the imaging unit, and the second numerical aperture of the optical lens system and the second imaging modality of the imaging unit, and wherein the optical guide means comprises a photonic crystal fibre.

10. An imaging system comprising:

a catheter having an optical lens system, the optical lens system being situated at an end portion of the catheter and optically connected to optical guide unit configured to guide light through the catheter, the optical lens system having a numerical aperture which is changeable between a first numerical aperture and a second numerical aperture, said second numerical aperture being higher than said first numerical aperture, and an imaging unit being arranged for optical imaging in co-operation with the catheter, the imaging unit comprising a first imaging modality and a second imaging modality, wherein the first and second imaging modalities are optically connectable with the optical lens system of the catheter, wherein the imaging system is configured to change between imaging with the first numerical aperture of the optical lens system and the first imaging modality of the imaging unit, and the second numerical aperture of the optical lens system and the second imaging modality of the imaging unit, and wherein the first imaging modality is an optical coherence tomography imaging system.

11. An imaging system comprising:

a catheter having an optical lens system, the optical lens system being situated at an end portion of the catheter and optically connected to optical guide unit configured to guide light through the catheter, the optical lens system having a numerical aperture which is changeable between a first numerical aperture and a second numerical aperture, said second numerical aperture being higher than said first numerical aperture, and an imaging unit being arranged for optical imaging in co-operation with the catheter, the imaging unit comprising a first imaging modality and a second imaging modality, wherein the first and second imaging modalities are optically connectable with the optical lens system of the catheter, wherein the imaging system is configured to change between imaging with the first numerical aperture of the optical lens system and the first imaging modality of the imaging unit, and the second numerical aperture of the optical lens system and the second imaging modality of the imaging unit, and wherein the second imaging modality is a multi photon microscopy imaging system.

12. An imaging system comprising:

a catheter having an optical lens system, the optical lens system being situated at an end portion of the catheter and optically connected to optical guide unit configured to guide light through the catheter, the optical lens system having a numerical aperture which is changeable between a first numerical aperture and a second numerical aperture, said second numerical aperture being higher than said first numerical aperture, and an imaging unit being arranged for optical imaging in co-operation with the catheter, the imaging unit comprising a first imaging modality and a second imaging modality, wherein the first and second imaging modalities are optically connectable with the optical lens system of the catheter, wherein the imaging system is configured to change between imaging with the first numerical aperture of the optical lens system and the first imaging modality of the imaging unit, and the second numerical aperture of the optical lens system and the second imaging modality of the imaging unit, and wherein the second imaging modality is a confocal microscopy imaging system.

13. An imaging system comprising:

a catheter having an optical lens system, the optical lens system being situated at an end portion of the catheter and optically connected to optical guide unit configured to guide light through the catheter, the optical lens system having a numerical aperture which is changeable between a first numerical aperture and a second numerical aperture, said second numerical aperture being higher than said first numerical aperture, and an imaging unit being arranged for optical imaging in co-operation with the catheter, the imaging unit comprising a first imaging modality and a second imaging modality, wherein the first and second imaging modalities are optically connectable with the optical lens system of the catheter, wherein the imaging system is configured to change between imaging with the first numerical aperture of the optical lens system and the first imaging modality of the imaging unit, and the second numerical aperture of the optical lens system and the second imaging modality of the imaging unit, and wherein the first and second imaging modalities utilize a common radiation source.

14. A catheter having an optical lens system, the optical lens system being situated at an end portion of the catheter and optically connected to optical a guide unit configured to guide light through the catheter, the optical lens system having a numerical aperture which is changeable between a first numerical aperture and a second numerical aperture, said second numerical aperture being higher than said first numerical aperture, wherein the catheter is further adapted to be optically connected to an associated imaging unit arranged for optical imaging in co-operation with the catheter, the imaging unit comprising a first imaging modality and a second imaging modality, wherein the first and second imaging modalities are optically connectable with the optical lens system of the catheter, and wherein the catheter comprises a first control unit configured to change the numerical aperture of the optical lens system between the first numerical aperture and the second numerical aperture, and the associated imaging unit comprises second control unit configured to change between imaging with the first and second imaging modalities of the imaging unit, said first and second control means further being arranged for mutual interaction with respect to change of imaging.

15. A method for imaging with an imaging system, the method comprising:

providing a catheter having an optical lens system, the optical lens system being situated at an end portion of the catheter and optically connected to optical guide means for guiding light through the catheter, the optical lens system having a numerical aperture which is changeable between a first numerical aperture and a second numerical aperture, said second numerical aperture being higher than said first numerical aperture, and providing an imaging unit being arranged for optical imaging in co-operation with the catheter, the imaging unit comprising a first imaging modality and a second imaging modality, both imaging modalities being optically connectable with the optical lens system of the catheter, wherein the method comprises changing between imaging with:

the first numerical aperture of the optical lens system and the first imaging modality of the imaging unit, and the second numerical aperture of the optical lens system and the second imaging modality of the imaging unit, and changing the numerical aperture of the optical lens system between the first numerical aperture and the second numerical aperture using a first control unit of the catheter; and changing between imaging with the first and the second imaging modalities using a second control unit of the imaging unit, wherein the first and second control units are configured for mutual interaction with respect to change of the imaging.

* * * * *